United States Patent [19]

Jurgutis

[11] Patent Number: 4,467,478

[45] Date of Patent: Aug. 28, 1984

[54] HUMAN LIGAMENT REPLACEMENT

[76] Inventor: John A. Jurgutis, 506 Georgina Ave., Santa Monica, Calif. 90402

[21] Appl. No.: 419,712

[22] Filed: Sep. 20, 1982

[51] Int. Cl.³ .............................................. A61F 1/00
[52] U.S. Cl. .......................................... 3/1; 128/92 C
[58] Field of Search ......................................... 3/1, 1.4

[56] References Cited

U.S. PATENT DOCUMENTS 3,463,158  8/1969  Schmitt et al. ............................... 3/1
3,938,524  2/1976  Sparks ...................................... 3/1.4
3,974,526  8/1976  Dardik et al. ............................. 3/1.4

*Primary Examiner*—Richard J. Apley
*Assistant Examiner*—David J. Isabella

*Attorney, Agent, or Firm*—Ralph B. Pastoriza

[57] ABSTRACT

The ligament replacement is obtained by taking a tendon from an animal of appropriate size to function as the substitute for the particular human ligament to be replaced. This tendon is cut to an appropriate length and immersed in a fixing solution such as glutaraldehyde for a sufficient length of time to bind the tissue. The tendon is wrapped in a protective covering and absorbable sutures are passed through the tendon to provide openings. After the tendon is grafted to the human portions formerly connected to the ligament to be replaced and healing has begun, scar tissue can then migrate into the openings left by the absorbable sutures to increase the strength and the securement of the tendon to the bone portions.

7 Claims, 3 Drawing Figures

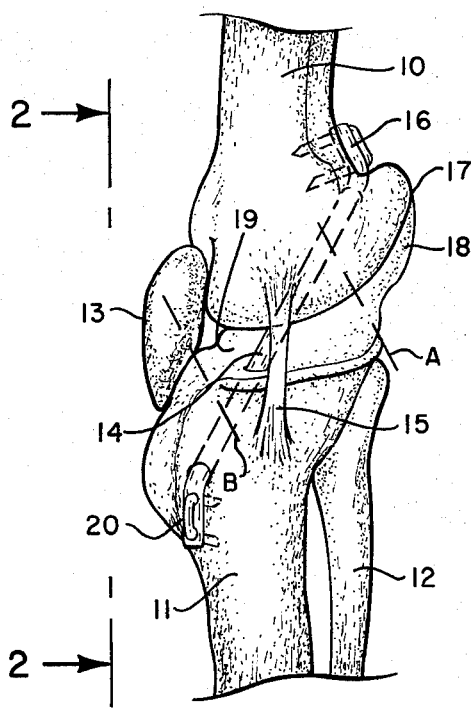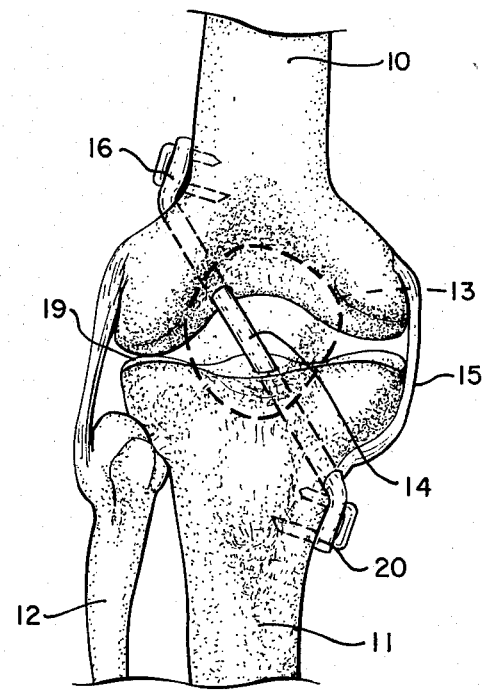
FIG. 1  FIG. 2
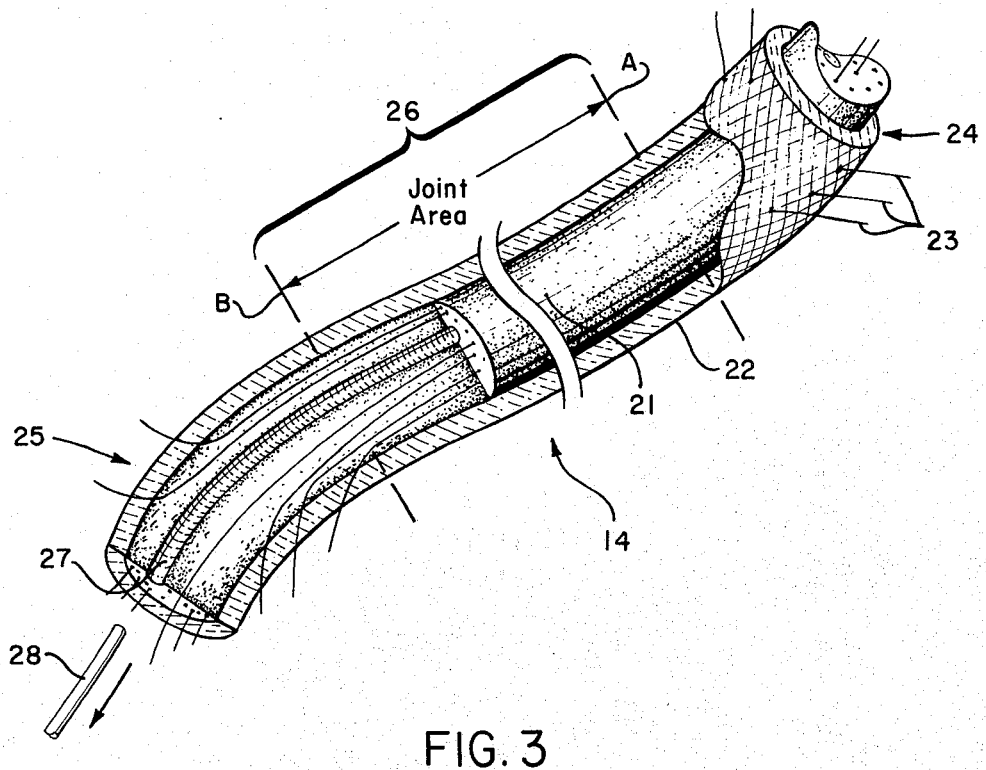
FIG. 3

HUMAN LIGAMENT REPLACEMENT

FIELD OF THE INVENTION

This invention relates generally to orthopedics and more particularly to a human ligament replacement and method of making the same.

BACKGROUND OF THE INVENTION

It is known to replace damaged human ligaments by a synthetic material such as a synthetic polyester fiber made from methyl terephthalate and ethylene glycol, commercially produced under the trademark "Dacron". Such synthetic substitutes are effective for a time, but after a long period, they tend to disintegrate.

Non-synthetic ligament substitutes have been used such as a tendon taken from an animal and appropriately fixed in a fixing solution such as glutaraldehyde. As in the case of synthetic substitutes, however, it is found that tendons similarly do not last a sufficient length of time as to be really effective.

BRIEF DESCRIPTION OF THE PRESENT INVENTION

With the foregoing considerations in mind, I have discovered an improved human ligament replacement or substitute which combines some of the more useful features of prior art substitutes such as discussed above without exhibiting the disadvantages thereof.

More particularly, in accord with the method of making the human ligament replacement, I use an animal tendon of appropriate thickness to function as a substitute for the particular human ligament to be replaced, this tendon being cut to an appropriate length and immersed in a fixing solution such as glutaraldehyde.

As mentioned heretofore, the above process is already known to provide a ligament replacement. However, in addition to the above, I then wrap the tendon in a protective covering which may comprise, for example, a piece of pericardium or a synthetic mesh such as "dacron". Thereafter, I pass absorbable sutures through the tendon to provide openings therein.

With the further treated tendon as described above, the same can now be grafted to the human bone portions formerly connected to the ligament to be replaced. After healing has begun, scar tissue can then migrate into the openings left by the absorbable sutures to increase the strength of the securement of the tendon to the bone portions.

A very effective human ligament replacement results by utilizing the tendon treated as described. The protective covering whether of pericardium or synthetic absorbant material inhibits disintegration of the tendon and the openings provided by the absorbable sutures provide for a very secure grafting of the tendon to the bone portions.

BRIEF DESCRIPTION OF THE DRAWINGS

A better understanding of this invention will be had by referring to the accompanying drawings of which:

FIG. 1 is a side elevational view of a typical knee joint illustrating a normal ligament along with a ligament replacement product in accord with the present invention;

FIG. 2 is a front elevational view of the knee joint illustrated in FIG. 1 looking in the direction of the arrows 2—2 but showing the knee cap in phantom lines; and FIG. 3 is an enlarged fragmentary broken away view partly in cross section of the ligament replacement product illustrated in FIGS. 1 and 2.

The present invention can best be understood by considering a specific example of a human ligament replacement. Towards this end, the anterior cruciate ligament of the human knee joint has been selected as a specific example, the knee joint being illustrated generally in FIGS. 1 and 2.

More particularly, and with reference to FIG. 1 there is shown in the upper portion of the drawing the lower end of the femur bone 10 connecting to the upper end of the tibia bone 11. Also shown is the fibula 12 and the patella or knee cap 13.

The fumur and tibia are held together by various ligaments. In FIG. 1, the anterior cruciate ligament has been replaced by the ligament replacement product of the invention designated genereally by the numeral 14. Also shown is a normal ligament 15. The ligament replacement product 14 has its upper end fastened as by staple 16 to a bone portion of the lower femur close to the medial condyle 17 and the lateral condyle 18. The replacement 14 extends from this first attachment point through the knee joint 19 and over the anterior intercondylar fossa of the tibia 11. Its other end is attached as by staple 20 to a bone portion of the tibia as shown.

With reference to FIG. 2, the replacement 14 is seen to pass central of the knee joint 19 behind or under the knee cap 13, shown in phantom lines. The original ligament is constantly working and is very important in coupling the femur and tibia and replacement of this particular ligament has been very difficult in the past. It is for this reason that the particular example is chosen but, as stated, any ligament can be replaced in accord with the teachings of the present invention.

Referring now to FIG. 3, there is shown the ligament replacement 14 of FIGS. 1 and 2 and the manner in which the replacement product itself is made.

As briefly described heretofore, the replacement is made up by first obtaining a tendon from an animal such as a cow, sheep or pig. The selected tendon will depend upon the particular ligament to be replaced. In other words, a tendon of appropriate diameter or thickness is chosen.

After the tendon has been obtained from the animal, it is cut to an appropriate length depending again upon the particular human ligament to be replaced.

Next, the tendon is immersed in a fixing solution, preferably a gluteraldehyde 2% solution for a sufficient length of time; for example, 48 hours to assure that the tissue is appropriately bound.

After appropriate fixing of the tendon which is analogous to tanning of leather, the tendon is wrapped in an appropriate protective covering. This covering may comprise a piece of a cow's pericardium. Alternatively, and for certain applications, rather than wrapping the tendon in a piece of pericardium, a synthetic mesh or porous type material could be used. One example would be "dacron". In FIG. 3, the animal tendon after having been fixed in the gluteraldehyde solution is shown at 21 and the wrapping thereabout at 22.

In accord with a next step in the method, absorbable type sutures are passed through the tendon to provide openings therein. These sutures are indicated in FIG. 3 at 23 entering one side and end area 24 to pass longitudinally through the tendon 21 and exit out the opposite side and end areas 25. Between the opposite end areas 24 and 25 described, there remains central side surfaces extending over a substantial longitudinal length indicated by the numeral 26 in FIG. 3 which are free of ingoing sutures and outgoing sutures. This longitudinal central area is demarked between the dashed lines A and B and constitute that portion of the tendon passing through the joint area between the bones formerly connected by the ligament being replaced.

Thus, with reference to FIG. 1, the joint area 19 between the dashed lines A and B is the particular joint area through which the longitudinal portion 26 of the tendon 21 in FIG. 3 passes.

The replacement ligament in the form of the tendon with the wrapping and sutures described in FIG. 3 may optionally be further treated by forming at least one longitudinal channel such as indicated at 27 in FIG. 3 through the tendon by passing a wire, a portion of which is indicated at 28, through the tendon prior to immersing of the tendon in the fixing solution. In other words, the channel 27 in the tendon 21 of FIG. 3 would be provided prior to the fixing or binding of the tendon tissues in the solution of the glutaraldehyde, this channel permitting greater penetration of the fixing solution within the tendon.

In the actual replacement, the damaged tendon of FIGS. 1 and 2 would be surgically removed and the replacement tendon 14 described in FIG. 3 substituted therefor. In this respect, the opposite end areas 24 and 25 would be affixed by the staples 16 and 20 described in FIG. 1, to the bone portions formerly connected to the original ligament. Entering and exiting sutures 23 described in FIG. 3 will lie outside the dashed lines A and B in FIG. 1 so that the portion of the tendon passing through the joint 19 is free of these sutures.

After the ends 24 and 25 of the tendon of FIG. 3 have been grafted to the human bone portions 16 and 20 in FIG. 1 and healing has begun, scar tissue can migrate into the various openings left by the absorbable sutures 23 and thus increase the strength and the securement of the tendon to the bone portions.

I have established by experiments with animals that ligament replacement in the form of the tendon described in FIG. 3 is extremely effective, will not become dislocated nor disintegrate and far surpasses any prior art ligament substitute available at the present time in overall effectiveness.

As mentioned heretofore, while the present invention has been described with respect to the replacement of a knee joint ligament, the replacement tendon can be appropriately sized as a substitute for other ligaments in the human body.

I claim:

1. A method of making a human ligament replacement including the steps of:
   (a) obtaining an animal tendon of appropriate thickness to function as a substitute for the particular human ligament to be replaced;
   (b) cutting the tendon to an appropriate length as determined by the ligament to be replaced;
   (c) immersing the tendon in a fixing solution for a sufficient length of time to bind the tendon tissue;
   (d) wrapping the tendon with a protective covering; and
   (e) passing absorbable sutures through the tendon to provide openings therein whereby after the tendon ends are grafted to the human bone portions formerly connected to the ligament being replaced and healing has begun, scar tissue can migrate into the openings left by the absorbable sutures to increase the strength and the securement of the tendon to said bone portions.

2. The method of claim 1, including the step of forming at least one longitudinal channel through said tendon by passing a wire therethrough prior to immersing of the tendon in said fixing solution.

3. The method of claim 1, in which said fixing solution is glutaraldehyde.

4. The method of claim 1, in which said protective covering is a piece of a pericardium.

5. The method of claim 1, in which said protective covering is a synthetic porous material.

6. A human ligament replacement comprising, in combination:
   (a) an animal tendon whose tissue has been bound by immersion in a fixing solution;
   (b) a protective covering wrapped about said tendon; and
   (c) absorbable sutures passing longitudinally through the tendon whereby after the tendon ends are grafted to the human bone portions formerly connected to the ligament being replaced and healing has begun, scar tissue can migrate into the openings left by the absorbable sutures to increase the strength and the securement of the tendon to said bone portions.

7. A human ligament replacement according to claim 6, in which said sutures extend into end and side areas adjacent to one end of the tendon and pass out end and side areas adjacent to the opposite end of the tendon to leave central side surfaces extending over a substantial longitudinal length of the tendon between its ends free of any incoming or outgoing sutures, said central side surfaces constituting that portion of the tendon passing through a joint area between said bone portions.

* * * * *